United States Patent
Nijkamp et al.

(10) Patent No.: US 11,523,869 B2
(45) Date of Patent: Dec. 13, 2022

(54) METHOD AND SYSTEM OF PROVIDING VISUAL INFORMATION ABOUT A LOCATION AND SHAPE OF A TUMOUR UNDER A BODY SURFACE OF A HUMAN OR ANIMAL BODY

(71) Applicant: STICHTING HET NEDERLANDS KANKER INSTITUUT-ANTONI, Amsterdam (NL)

(72) Inventors: Jasper Albertus Nijkamp, Amsterdam (NL); Koert Frans Dirk Kuhlmann, Amsterdam (NL); Jan-Jakob Sonke, Amsterdam (NL); Theodoor Jacques Marie Ruers, Amsterdam (NL)

(73) Assignee: Stichting Het Nederlands Kanker Instituut—Antoni van Leeuwenhoek Ziekenhuis, Amsterdam (NL)

( * ) Notice: Subject to any disclaimer, the term of this patent is extended or adjusted under 35 U.S.C. 154(b) by 743 days.

(21) Appl. No.: 15/777,248

(22) PCT Filed: Nov. 18, 2016

(86) PCT No.: PCT/NL2016/050806
§ 371 (c)(1),
(2) Date: May 18, 2018

(87) PCT Pub. No.: WO2017/086789
PCT Pub. Date: May 26, 2017

(65) Prior Publication Data
US 2018/0333210 A1 Nov. 22, 2018

(30) Foreign Application Priority Data
Nov. 20, 2015 (NL) ...................... 2015835

(51) Int. Cl.
*A61B 34/20* (2016.01)
*A61B 5/00* (2006.01)
(Continued)

(52) U.S. Cl.
CPC ............ *A61B 34/20* (2016.02); *A61B 5/0077* (2013.01); *A61B 5/062* (2013.01); *A61B 5/065* (2013.01);
(Continued)

(58) Field of Classification Search
CPC ..... A61B 8/0841; A61B 8/0825; A61B 34/20; A61B 2034/2055; A61B 2034/2051;
(Continued)

(56) References Cited

U.S. PATENT DOCUMENTS 5,868,673 A   2/1999  Vesely
6,120,465 A * 9/2000  Guthrie .................. A61B 90/36
                                                   600/587
(Continued)

FOREIGN PATENT DOCUMENTS

WO   2015069106 A1   5/2015

OTHER PUBLICATIONS

Keil Matthias et al: A Real-Rime Online Video Overlay Navigation System for Minimally Invasive Laparoscopic Tumor Resection. Medical Imaging 2011: Visualization, Image-Guided Procedures, and Modeling, edited by Kenneth H. Wong, David R. Holmes III, Proc. of SPIE vol. 7964, 79516. (Year: 2011).*
(Continued)

*Primary Examiner* — Christopher Koharski
*Assistant Examiner* — Richmond J Van Winter
(74) *Attorney, Agent, or Firm* — N.V. Nederlandsch Octrooibureau (57) ABSTRACT

In a method and system for providing visual information about a tumour location in human or animal body, an
(Continued)

electromagnetic tumour sensor is provided in the tumour and tracked to determine its location in space, which is mapped to a tumour model. A surgical tool sensor is provided on a surgical tool, and tracked to determine its location in space, which is mapped to a surgical tool model. The body is scanned to obtain information about an anatomical structure. A reference sensor is provided on the body, and tracked to determine its location in space, which is mapped to the anatomical structure. A virtual image is displayed showing the tumour model, located with the at least one tumour sensor, in spatial relationship to the surgical tool model, located with the at least one surgical tool sensor, and the anatomical structure, located with the at least one reference sensor.

21 Claims, 6 Drawing Sheets

(51) Int. Cl.
| | | |
|---|---|---|
| | *A61B 5/06* | (2006.01) |
| | *A61B 6/00* | (2006.01) |
| | *A61B 8/08* | (2006.01) |
| | *G06T 7/70* | (2017.01) |
| | *A61B 6/12* | (2006.01) |
| | *A61B 90/00* | (2016.01) |

(52) U.S. Cl.
CPC ............ *A61B 6/502* (2013.01); *A61B 8/0825* (2013.01); *A61B 8/0841* (2013.01); *G06T 7/70* (2017.01); *A61B 6/12* (2013.01); *A61B 6/5217* (2013.01); *A61B 2034/2051* (2016.02); *A61B 2034/2055* (2016.02); *A61B 2034/2057* (2016.02); *A61B 2090/364* (2016.02); *A61B 2090/373* (2016.02); *A61B 2090/374* (2016.02); *A61B 2090/3762* (2016.02); *A61B 2562/0238* (2013.01)

(58) Field of Classification Search
CPC ............ A61B 2034/2057; A61B 6/502; A61B 6/5217; A61B 6/12; A61B 5/0077; A61B 5/062; A61B 5/065; A61B 2090/374; A61B 2090/3762; A61B 2090/373; A61B 2090/364; A61B 2562/0238; G06T 7/70
See application file for complete search history.

(56) References Cited

U.S. PATENT DOCUMENTS

| | | | | |
|---|---|---|---|---|
| 2009/0216114 | A1* | 8/2009 | Gorges | A61B 90/36 600/425 |
| 2013/0096392 | A1* | 4/2013 | Adams | A61B 5/14546 600/301 |
| 2015/0051480 | A1* | 2/2015 | Hwang | A61B 5/113 600/424 |
| 2016/0048958 | A1* | 2/2016 | Miga | A61B 8/58 382/131 |
| 2016/0143693 | A1* | 5/2016 | Yilmaz | A61B 6/12 606/130 |

OTHER PUBLICATIONS

Amish P Shah et al: Expanding the use of real time electromagnetic tracking in radiaton oncology. Journal of Applied Clinical Medical Physics, vol. 12, No. 4, Fall 2011. (Year: 2011).*
Amish P Shah et al.: Expanding the use of real time electromagnetic tracking in radiation oncology. Journal of Applied Clinical Medical Physics, vol. 12, No. 4, Fall 2011. (Year: 2011).*
VARIAN Medical Systems: 'Real-time Motion Tracking for Real-Life Results—The Calypso System'; Oct. 2012.
Grunert et al., "Computer-aided navigation in neurosurgery", Neurosurg Rev 2003; 26(2):73-99-1.
Senft et al., "Intraoperative magnetic resonance imaging in the surgical treatment of cerebral metastases", J Surg Oncol 2010;101(5):436-41. Doi: 10.1002/jso.21508.
Langø et al., "Navigation in laparoscopy—prototype research platform for improved image-guided surgery", Minim Invasive Ther Allied Technol 2008;17(1):17-33. Doi: 10.1080/13645700701797879.
Aschendorff et al., "Radiologically assisted navigation in cochlear implantation for X-linked deafness malformation", Cochlear Implants Int 2009;10 Suppl 1:14-8. Doi: 10.1002/cii.379.
Wong et al., "Use of Computer Navigation in Orthopedic Oncology", Curr Surg Reports 2014;2:47. Doi: 10.1007/s40137-014-0047-0.
Maier-Hein et al., "Standardized assessment of new electromagnetic field generators in an interventional radiology setting", Med Phys 2012;39(6):3424-34. Doi: 10.1118/1.4712222.
Su et al., "Augmented reality during robot-assisted laparoscopic partial nephrectomy: toward real-time 3D-CT to stereoscopic video registration", Urology, vol. 73, No. 4, pp. 896-900, Apr. 2009.
Sugimoto et al., "Image overlay navigation by markerless surface registration in gastrointestinal, hepatobiliary and pancreatic surgery", Journal of hepato-biliary-pancreatic sciences, vol. 17, No. 5, pp. 629-636, Sep. 2010.
Volonté et al., "Augmented reality and image overlay navigation with OsiriX in laparoscopic and robotic surgery: not only a matter of fashion", Journal of hepato-biliary-pancreatic sciences, vol. 18, No. 4, pp. 506-509, Jul. 2011.
Park et al., "Liver motion during cone beam computed tomography guided stereotactic body radiation therapy", Medical physics, vol. 39, No. 10, pp. 6431-6442, Oct. 2012.
Uneri et al., "TREK: an integrated system architecture for intraoperative conebeam CT-guided surgery", International journal of computer assisted radiology and surgery, vol. 7, No. 1, pp. 159-173, Jan. 2012.
Hummel et al., "Design and application of an assessment protocol for electromagnetic tracking systems", Medical physics, vol. 32, No. 7, pp. 2371-2379, Jul. 2005.
Winne et al., "Overlay visualization in endoscopic ENT surgery", International journal of computer assisted radiology and surgery, vol. 6, No. 3, pp. 401-406, May 2011.
Balter et al., "Accuracy of a wireless localization system for radiotherapy", International journal of radiation oncology, biology, physics, vol. 61, No. 3, pp. 933-937, Mar. 2005.
Dindo et al., "Classification of surgical complications: a new proposal with evaluation in a cohort of 6336 patients and results of a survey", Annals of surgery, vol. 240, No. 2, pp. 205-213, Aug. 2004.
Gray et al., "Randomized prospective evaluation of a novel technique for biopsy or lumpectomy of nonpalpable breast lesions: radioactive seed versus wire localization", Ann. Surg. Oncol., vol. 8, No. 9, pp. 711-715, Oct. 2001.
Hughes et al., "A multi-site validation trial of radioactive seed localization as an alternative to wire localization", Breast J., vol. 14, No. 2, pp. 153-157.
Gray et al., "Radioactive seed localization of nonpalpable breast lesions is better than wire localization", Am. J. Surg., vol. 188, No. 4, pp. 377-380, Oct. 2004.
Lovrics et al., "A multicentered, randomized, controlled trial comparing radioguided seed localization to standard wire localization for nonpalpable, invasive and in situ breast carcinomas", Ann. Surg. Oncol., vol. 18, No. 12, pp. 3407-3414, Nov. 2011.
Wu et al., "Intraoperative navigation for minimally invasive resection of periarticular and pelvic tumors", Orthopedics 2011; 34(5):372.
Ty et al., "Computer-assisted navigation in bone tumor surgery: seamless workflow model and evolution of technique", Clin Orthop Relat Res 2010; 468(11):2985-2991.
Zwingmann et al., "Computer-navigated iliosacral screw insertion reduces malposition rate and radiation exposure", Clin Orthop Relat Res 2009; 467(7):1833-1838.

(56) References Cited

OTHER PUBLICATIONS

Kubben et al., "Intraoperative MRI-guided resection of glioblastoma multiforme: a systematic review", Lancet Oncol 2011; 12(11):1062-1070.

Roetenberg et al., "Ambulatory position and orientation tracking fusing magnetic and inertial sensing", IEEE Trans. Biomed. Eng., vol. 54, No. 5, pp. 883-890, May 2007.

Schepers et al., "Ambulatory human motion tracking by fusion of inertial and magnetic sensing with adaptive actuation", Med. Biol. Eng. Comput., vol. 48, No. 1, pp. 27-37, Jan. 2010.

Schepers et al., "Stochastic magnetic measurement model for relative position and orientation estimation", Meas. Sci. Technol., vol. 21, No. 6, p. 065801, Jun. 2010.

Roetenberg et al., "Estimating body segment orientation by applying inertial and magnetic sensing near ferromagnetic materials", IEEE Trans. Neural Syst. Rehabil. Eng., vol. 15, No. 3, pp. 469-471, Sep. 2007.

Keil Matthias et al: A Real-Rime Online Video Overlay Navigation System for Minimally Invasive Laparoscopic Tumor Resection. Medical Imaging 2011: Visualization, Image-Guided Procedures, and Modeling, edited by Kenneth H. Wong, David R. Holmes III, Proc. of SPIE vol. 7964, 79516.

Amish P Shah et al: Expanding the use of real time electromagnetic tracking in radiaton oncology. Journal of Applied Clinical Medical Physics, vol. 12, No. 4, Fall 2011.

\* cited by examiner

METHOD AND SYSTEM OF PROVIDING VISUAL INFORMATION ABOUT A LOCATION AND SHAPE OF A TUMOUR UNDER A BODY SURFACE OF A HUMAN OR ANIMAL BODY

FIELD OF THE INVENTION

The invention relates to the field of imaging a tumour in a human or animal body, and more specifically to a method and system for providing visual information about a location of the tumour. The invention further relates to a computer program and computer program product for data generation and processing operations, and operating systems relating to the method and system of the invention.

BACKGROUND OF THE INVENTION

Reference U.S. Pat. No. 5,868,673 A discloses a system for carrying out surgery on a bodily structure. A threedimensional tracking and imaging system is used to obtain an accurate position of an instrument as it is maneuvered by an operator, and to mark a location on the subject bodily structure.

As an example, tagging of a tumor located in a breast comprises affixing a plurality of external reference transducers to the surface of the breast. The reference transducers provide a stereotactic external reference frame for an interactive 3-D display of the movement of a probe during insertion of an internal transducer. The tumour is tagged by inserting an internal ultrasonic transducer into the tumour during conventional mammography.

A drawback of the system according to said reference is that in an operation or other treatment only a reference point indicating a location of the tumour can be found, so that a surgeon or other physician has little guidance as to the actual location of treatment, and the amount of tissue to be removed in the operation or other treatment.

Keil, Matthias et al.: "A Real-Time Online Video Overlay Navigation System for Minimally Invasive Laparoscopic Tumor Resection", Medical Imaging 2011: Visualization, Image-Guided Procedures, and Modeling, SPIE, 1000 20*th* St. Bellingham Wash. 98225-6705 USA, Part 7964, No. 1, Mar. 3, 2011, pages 1-8, discloses a real-time navigation system for computer assisted surgery with tracking of tumour position and orientation during surgery, using a system based on ultrasound to CT registration and electromagnetic tracking.

SUMMARY OF THE INVENTION

It would be desirable to provide an improved method and system for providing enhanced visual information about a location of a tumour under a body surface of a human or animal body.

To better address this concern, in a first aspect of the invention a method of providing visual information about a location of a tumour under a body surface of a human or animal body is provided. The method comprises the steps of:

at least one electromagnetic tumour sensor interacting with a tumour sensor tracking system to determine an individual location of the tumour sensor in space;

determining a digital volumetric tumour model representative of the tumour;

mapping each tumour sensor location to the tumour model;

providing at least one surgical tool provided with at least one surgical tool sensor, each surgical tool sensor interacting with a surgical tool sensor tracking system to determine an individual location of the surgical tool sensor in space, wherein the surgical tool sensor tracking system is calibrated to provide locations in a first coordinate system, and wherein the tumour sensor tracking system is calibrated to provide locations in a second coordinate system;

determining a digital surgical tool model representative of the surgical tool;

mapping each surgical tool sensor location to the surgical tool model;

scanning the human or animal body to obtain information about at least one anatomical structure in the human or animal body in a vicinity of the tumour;

at least one reference sensor interacting with a reference sensor tracking system to determine an individual location of the reference sensor in space, wherein the reference sensor tracking system is calibrated to provide locations in a third coordinate system;

mapping each reference sensor location to at least one anatomical structure in the human or animal body;

determining the location of each tumour sensor in space;

determining the location of each surgical tool sensor in space;

determining the location of each reference sensor in space;

assembling, based on the first and second coordinate systems, a virtual image showing the tumour model, as located with the at least one tumour sensor, in a spatial relationship to the surgical tool model, as located with the at least one surgical tool sensor; and assembling, based on the third coordinate system, the virtual image further to show the at least one anatomical structure, as located with the at least one reference sensor, in a spatial relationship to the tumour model, as located with the at least one tumour sensor, and/or in a spatial relationship to the surgical tool model, as located with the at least on surgical tool sensor.

According to the invention, a real-time or quasi real-time location, i.e. position and/or orientation, of a volume of interest, i.e. the tumour, is obtained and thereby the tumour, represented as a volumetric tumour model, is included in a virtual image. Additionally, a real-time or quasi real-time location, i.e. position and/or orientation, of a surgical tool may be obtained and thereby the surgical tool, represented by the surgical tool model, may be included in the virtual image.

The digital tumour model may be defined using information obtained from an imaging process.

Herein, a surgical tool comprises any tool of which at least part is intended to enter under the body surface of a human or animal patient. The digital surgical tool model may be a threedimensional, 3D, (volumetric) model, a twodimensional, 2D, (plane) model, a onedimensional, 1D, (line) model, or a zerodimensional, 0D, (point) model, depending e.g. on the physical embodiment of the actual surgical tool, or a part thereof, and/or its function.

The actual location in space of the tumour under a body surface of a human or animal body is inferred from the location of the at least one tumour sensor in space, where the tumour sensor previously may have been provided in, or in the vicinity of, or in close proximity to, a tumour in the human or animal body. The tumour sensor is provided such that its spatial position and/or orientation closely matches the spatial position and/or orientation of the tumour. The actual position in space of the surgical tool is inferred from the location of the at least one surgical tool sensor in space, where the surgical tool sensor may be provided in or on the surgical tool. In the virtual image, by displaying the volumetric tumour model and the volumetric surgical tool model in a spatial relationship as determined by the locations of the at least one tumour sensor and the at least one surgical tool sensor in space, the location and extension of the tumour is shown with respect to the location and extension of the surgical tool. Thus, a surgeon or other physician performing an operation or other local treatment under the surface of a human or animal body has the virtual image at his or her disposal showing in real-time or quasi real-time the progress of the operation or treatment.

Herein, the expression 'real-time' implies that the determination of locations and showing the tumour model in spatial relationship to the surgical tool model in the virtual image follows actual movement of the at least one tumour sensor and the at least one surgical tool sensor virtually without time delay, in particular within 1 to 2 seconds. The expression 'quasi real-time' implies that a small time delay, e.g. between 2 to 10 seconds, in particular between 2 and 5 seconds, is involved between the actual movement of the at least one tumour sensor and the at least one surgical tool sensor, and the determination of locations and showing the tumour model in spatial relationship to the surgical tool model in the virtual image.

In the virtual image, all locations may be shown in one coordinate system, on the same scale, and registered to each other. This is an important step forward in providing accurate guidance for a surgeon or other physician to perform a tumour operation or other local treatment.

The actual location in space of the at least one anatomical structure in the human or animal body is inferred from the location of the at least one reference sensor in space, where the reference sensor previously may have been provided on a surface of, or in the human or animal body.

It is noted that the first, second and third coordinate systems may be all the same, or at least one of them may be different from at least one of the others, as long as they are registered to each other when assembling a virtual image showing the tumour model in a spatial relationship to the surgical tool model. Herein, the expression 'coordinate system' denotes a system of coordinates fixed in space.

In an embodiment of the method, the at least one surgical tool sensor is an electromagnetic surgical tool sensor, and the surgical tool sensor tracking system may be the same as the tumour sensor tracking system. Since the surgical tool, in use, may be moved to under the surface of a human or animal body, the application of at least one electromagnetic surgical tool sensor on or in the surgical tool has the advantage of being trackable both above and under the surface of the human or animal body, without loss of continuity of locating.

In an embodiment of the method, the at least one surgical tool sensor is an optical surgical tool sensor, and the surgical tool sensor tracking system is an optical tracking system comprising at least one camera. Such an embodiment can be used when there practically always is a line of sight between the camera and the at least one surgical tool sensor. The optical tool sensor may be passive (e.g. reflective) or active (e.g. comprising a source of radiation that can be detected by the camera). The optical tool sensor may be provided with, or provide, an optically detectable pattern such as to distinguish between different optical surgical tool sensors.

In an embodiment of the method, the at least one reference sensor is an electromagnetic reference sensor, and the reference sensor tracking system is the same as the tumour sensor tracking system.

In an embodiment of the method, the at least one reference sensor is an optical reference sensor, and the reference sensor tracking system is an optical tracking system comprising at least one camera.

In an embodiment of the method, the step of scanning the human or animal body to obtain information about at least one anatomical structure in the human or animal body in a vicinity of the tumour is repeated at least once in combination with the step of determining the location of each tumour sensor in space. This may be done during an operation or other treatment.

In an embodiment of the method, the at least one tumour sensor further is configured to interact with the tumour sensor tracking system to determine an individual orientation of the tumour sensor in space.

In an embodiment of the method, the at least one surgical tool sensor further is configured to interact with the surgical tool sensor tracking system to determine an individual orientation of the surgical tool sensor in space.

In an embodiment of the method, the at least one reference sensor further is configured to interact with the reference sensor tracking system to determine an individual orientation of the reference sensor in space.

In an embodiment, the method further comprises the step of:
assembling the virtual image further to show a scale of length, or a scaled distance between the tumour model and the surgical tool model.

In an embodiment, the method further comprises the step of:
assembling the virtual image further to show a scale of length, or a scaled distance between the tumour model and the anatomical structure.

In an embodiment, the method further comprises the step of:
assembling the virtual image further to show a scale of length, or a scaled distance between the tool model and the anatomical structure.

In a second aspect of the present invention, a system for providing visual information about a location of a tumour under a body surface of a human or animal body is provided. The system comprises:
at least one electromagnetic tumour sensor;
a tumour sensor tracking system, wherein each tumour sensor is configured to interact with the tumour sensor tracking system to determine an individual location of the tumour sensor in space;
a tumour model mapping component configured for mapping each tumour sensor location to a digital volumetric tumour model representative of the tumour;
a surgical tool provided with at least one surgical tool sensor;
a surgical tool sensor tracking system, wherein each surgical tool sensor is configured to interact with the surgical tool sensor tracking system to determine an individual location of the surgical tool sensor in space, wherein the surgical tool sensor tracking system is calibrated to provide locations in a first coordinate system, and wherein the tumour sensor tracking system is calibrated to provide locations in a second coordinate system;
an surgical tool mapping component configured for mapping each surgical tool sensor location to a digital surgical tool model representative of the surgical tool;

an anatomical structure information input component for receiving information about at least one anatomical structure in the human or animal body in a vicinity of the tumour;

at least one reference sensor;

a reference sensor tracking system, wherein each reference sensor is configured to interact with the reference sensor tracking system to determine an individual location of the reference sensor in space, wherein the reference sensor tracking system is calibrated to provide locations in a third coordinate system;

an anatomical structure mapping component configured for mapping each reference sensor location to the at least one anatomical structure in the human or animal body;

a tumour sensor locating component configured for determining the location of each tumour sensor in space;

a surgical tool sensor locating component configured for determining the location of each surgical tool sensor in space;

a reference sensor locating component configured for determining the location of each reference sensor in space, a display device; and a displaying component configured for displaying on the display device, based on the first and second coordinate systems, a virtual image assembled to show the tumour model, as located with the at least one tumour sensor, in a spatial relationship to the surgical tool model, as located with the at least one surgical tool sensor, wherein the displaying component is configured for assembling, based on the third coordinate system, the virtual image further to show the at least one anatomical structure, as located with the at least one reference sensor, in a spatial relationship to the tumour model, as located with the at least one tumour sensor, and/or in a spatial relationship to the surgical tool model, as located with the at least on surgical tool sensor.

In an embodiment of the system, the at least one tumour sensor is configured to communicate wirelessly or wired with the tumour sensor tracking system, and/or the at least one surgical tool sensor is configured to communicate wirelessly or wired with the surgical tool sensor tracking system and/or the at least one reference sensor is configured to communicate wirelessly or wired with the reference sensor tracking system.

In a third aspect of the present invention, a computer program is provided. The computer program comprises computer instructions which, when loaded in a processor, cause the processor to operate one or more of the tumour sensor tracking system, the surgical tool sensor tracking system, the tumour model mapping component, the surgical tool, the surgical tool mapping component, the tumour sensor locating component, the tool sensor locating component, the anatomical structure information input component, the reference sensor tracking system, the anatomical structure mapping component, the reference sensor locating component, the display device, and the displaying component of the system of the second aspect of the present invention.

In an embodiment, the computer program further comprises computer instructions which, when loaded in a processor, cause the processor to operate one or more of the anatomical structure information input component, the reference sensor tracking system, the anatomical structure mapping component, and the reference sensor locating component of the system of the third aspect of the present invention.

In a fourth aspect of the present invention, a computer program product is provided. The computer program product comprises a data carrier having the computer instructions of the computer program of the present invention stored therein.

These and other aspects of the invention will be more readily appreciated as the same becomes better understood by reference to the following detailed description and considered in connection with the accompanying drawings in which like reference symbols designate like parts.

DETAILED DESCRIPTION OF EMBODIMENTS

Figure 1:
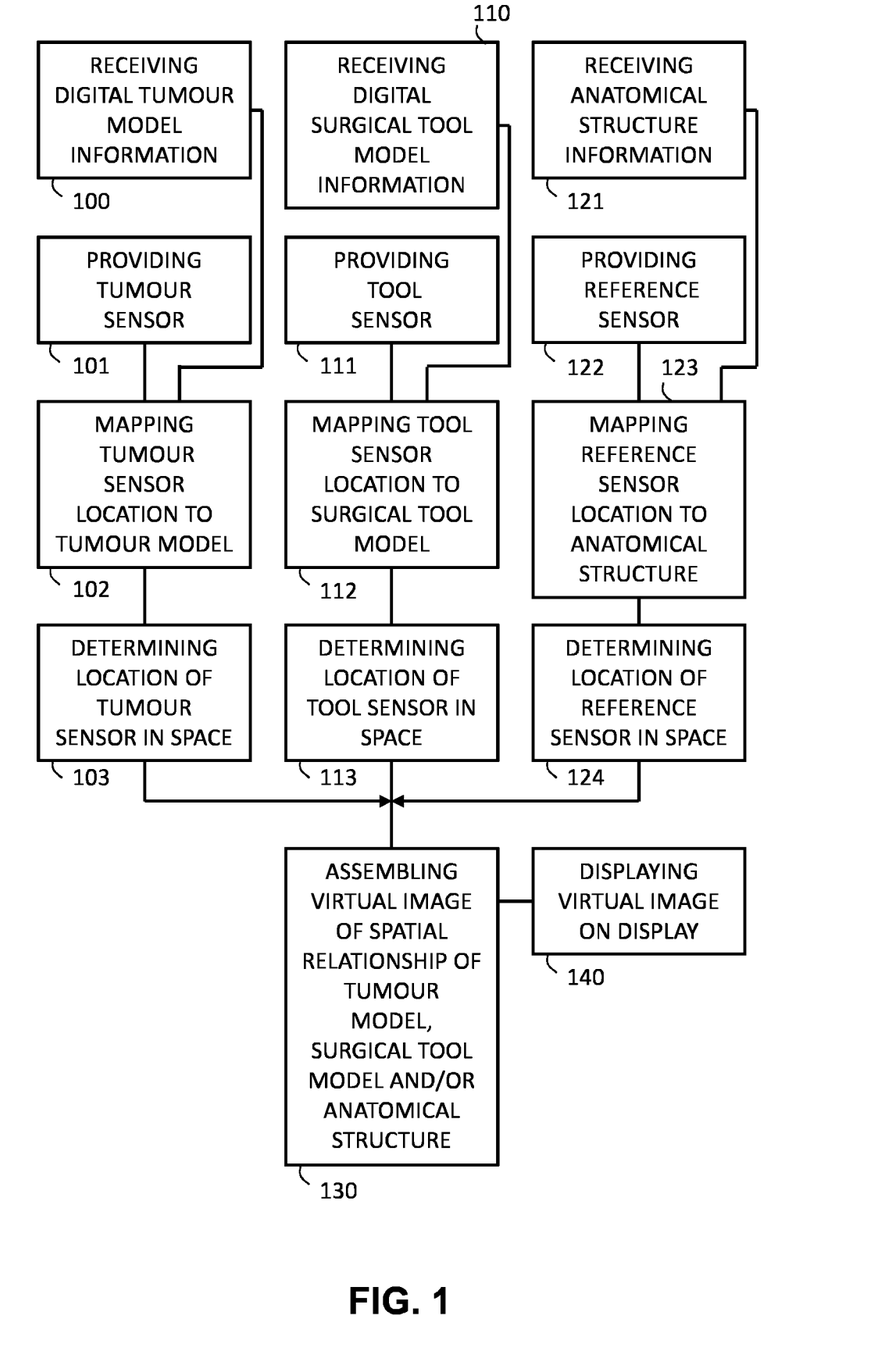
FIG. 1 depicts a flow diagram of steps performed in embodiments of a method of the present invention.

FIG. 1 depicts a flow diagram of steps performed in embodiments of a method of providing visual information about a location of a tumour under a body surface of a human or animal body of the present invention, in particular a location of a tumour with respect to a location of a surgical tool and/or a location of an anatomical structure of the human or animal body.

Herein, a component is taken be refer to software (a computer program), or a combination of software and hardware, for performing a specific function. The software comprises computer instructions to cause a processor to perform the function by data processing. The software may be stored in a non-transitory storage medium or memory.

According to step 100, information about a digital volumetric tumour model is received, e.g. from a database.

According to step 101, at least one electromagnetic tumour sensor is provided. Previously, the tumour sensor has been placed under a body surface of a human or animal body in the tumour, or in the vicinity of the tumour, or in close proximity to the tumour, to have a defined spatial relationship with the tumour. The process of providing the tumour sensor is not part of the present invention, and may be done by a surgeon or other physician during an invasive operation.

Each tumour sensor is configured to interact with a tumour sensor tracking system, as will be explained in more detail below, to determine an individual location of the tumour sensor in space.

According to step 102, following step 101, each tumour sensor location is mapped to a digital volumetric tumour model representative of the tumour. The tumour model comprises one or more volumes shaped to optimally represent the particular tumour, possibly including a further body tissue layer around the tumour. The mapping of a tumour sensor location entails defining a one-to-one relationship between a location on or in the tumour model and the specific tumour sensor, based on information of the actual location of the specific tumour sensor on the actual tumour.

According to step 103, following step 102, the location of each tumour sensor in space is determined, with the tumour sensor tracking system. This tumour sensor location in space provides the spatial location of a part of the tumour where the tumour sensor is located, and at the same time defines a virtual location of a part of the tumour model in an image to be displayed.

According to step 110, information about a digital surgical tool model is received, e.g. from a database.

According to step 111, at least one surgical tool is provided with at least one surgical tool sensor arranged on or in the surgical tool. Each surgical tool sensor is configured to interact with a surgical tool sensor tracking system, as will be explained in more detail below, to determine an individual location of the surgical tool sensor in space.

According to step 112, following step 111, each surgical tool sensor location is mapped to a digital surgical tool model representative of the surgical tool. The surgical tool model comprises a line (a onedimensional tool model), a plane having a defined edge shape (a twodimensional tool model), and/or one or more volumes (a threedimensional tool model) shaped to optimally represent the particular surgical tool. The mapping of a surgical tool sensor location entails defining a one-to-one relationship between a location on or in the surgical tool model and the specific surgical tool sensor, based on information of the actual location of the specific surgical tool sensor on the actual surgical tool.

According to step 113, following step 112, the location of each surgical tool sensor in space is determined, with the surgical tool sensor tracking system. This surgical tool sensor location in space provides the spatial location of a part of the surgical tool where the surgical tool sensor is located, and at the same time defines a virtual location of a part of the surgical tool model in an image to be displayed.

According to step 121, information about at least one anatomical structure in the human or animal body in a vicinity of the tumour is received, e.g. from a database, or from a scanning device.

According to step 122, at least one reference sensor is provided on the body surface of the human or animal body. Each reference sensor is configured to interact with a reference sensor tracking system, as will be explained in more detail below, to determine an individual location of the reference sensor in space.

According to step 123, following step 122, each reference sensor location is mapped to the at least one anatomical structure in the human or animal body. The anatomical structure comprises one or more volumes shaped to optimally represent the particular anatomical structure. The mapping of a reference sensor location entails defining a one-to-one relationship between a location on or in the anatomical structure and the specific reference sensor, based on information of the actual location of the specific reference sensor in relation to the actual anatomical structure.

According to step 124, following step 123, the location of each reference sensor in space is determined, with the reference sensor tracking system. This reference sensor location in space provides the spatial location of a part of the anatomical structure where the reference sensor is located, and at the same time defines a virtual location of a part of the anatomical structure in an image to be displayed.

The surgical tool tracking system, the tumour sensor tracking system, and the reference sensor tracking system are calibrated to provide locations in a first, second and third coordinate system, respectively.

According to step 130, a virtual image, based on said coordinate systems, of the at least one anatomical structure, as located with the at least one reference sensor, in a spatial relationship to the tumour model, as located with the at least one tumour sensor, and/or in a spatial relationship to the surgical tool model, as located with the at least on tool sensor is assembled, i.e. data are processed to provide image data to construct the virtual image.

According to step 140, the virtual image may be displayed on a display device to aid or guide a treating physician, e.g. a surgeon, in performing a tumour operation or other local treatment on a patient, in particular his or her human or animal body. The virtual image may further be assembled to show a scale of length, or a scaled distance between the tumour model and the surgical tool model, a scaled distance between the tumour model and the anatomical structure and/or a scaled distance between the tool model and the anatomical structure.

Herein, a spatial relationship between two elements is understood as a position of the elements relative to each other in space. In some embodiments, a spatial relationship may further involve an orientation of the elements relative to each other in space.

In some applications, only a spatial relationship between the tumour and the surgical tool needs to be visualized on a display device using the tumour model and the surgical tool model, and steps 121 to 124 may be omitted. In other applications, only a spatial relationship between the tumour and the anatomical structure needs to be visualized on a display device using the tumour model and the anatomical structure, and steps 111 to 113 may be omitted. In still other applications spatial relationships between the tumour, the surgical tool and the anatomical structure need to be visualized on a display device using the tumour model, the surgical tool model and the anatomical structure.

Steps 101, 102, 111, 112, 121, 122 and 123 may be performed pre-treatment or pre-operatively, while steps 103, 113, 124 and 130 may be performed during treatment or intra-operatively. In some applications, steps 121 and 123 may be performed also during treatment or intra-operatively, in particular when the body of the patient may be expected to move during treatment or intra-operatively.

Figure 2:
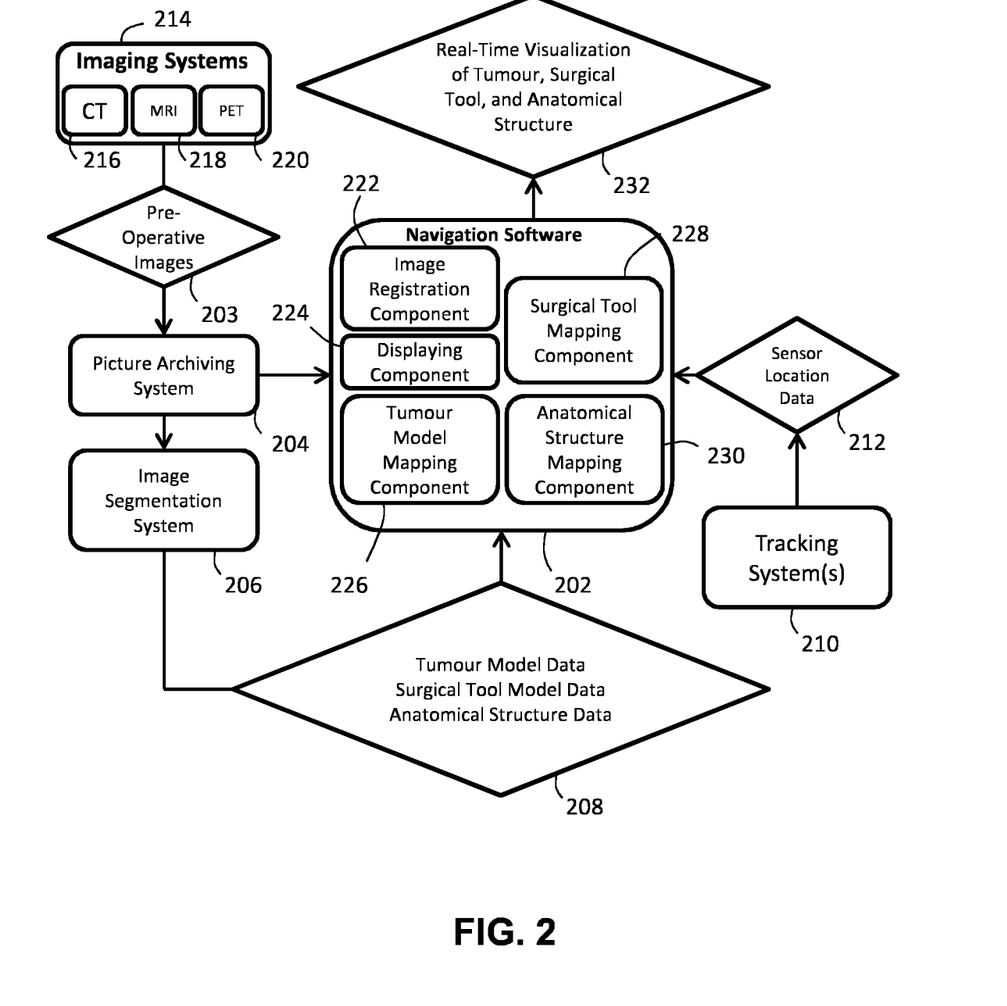
FIG. 2 depicts a diagram illustrating implementing aspects of a first embodiment of a method or system of the present invention.

FIG. 2 depicts a diagram illustrating implementing aspects of a first embodiment of a method or system of the present invention.

In an implementation of the method or system according to FIG. 2, navigation software 202 is used. The navigation software 202 receives input from three data sources.

A first data source for the navigation software 202 is a picture archiving system 204 containing image data of pre-operative images 203. The picture archiving system 204 receives image data representing pre-operative images 203 of anatomical structures from one or more imaging systems 214, such as a computer tomography, CT, imaging system 216, a magnetic resonance imaging, MRI, system 218, a positron emission tomography, PET, system 220, or any other appropriate system.

A second data source for the navigation software 202 is image segmentation system 206 comprising software providing image segmentation data 208 representing a tumour model, i.e. tumour model data, an anatomy model for a specific patient, i.e. anatomical structure data, and/or a surgical tool model, i.e. surgical tool model data.

A third data source for the navigation software 202 is a sensor tracking system 210, i.e. one or more of the tumour sensor tracking system, the surgical tool sensor tracking system, and the reference sensor tracking system, each tracking system providing sensor location data 212 of its respective sensor(s). The tumour sensor tracking system comprises a tumour sensor locating component configured for determining the location of each tumour sensor in space. The surgical tool sensor tracking system comprises a surgical tool sensor locating component configured for determining the location of each surgical tool sensor in space. The reference sensor tracking system comprises a reference sensor locating component configured for determining the location of each reference sensor in space.

It is noted here that a tumour sensor is an electromagnetic tumour sensor. A surgical tool sensor may be an electromagnetic surgical tool sensor or an optical surgical tool sensor. A reference sensor may be an electromagnetic reference sensor or an optical reference sensor.

An electromagnetic sensor may be a passive electromagnetic sensor, accommodating no power source and providing an individualized electromagnetic locating signal to a tracking system when interrogated by the tracking system, or an active electromagnetic sensor, accommodating a power source and actively providing an individualized electromagnetic locating signal to a tracking system without being interrogated by the tracking system.

An optical sensor may be a passive optical sensor, accommodating no power source and providing an individualized optical locating signal to a tracking system when receiving light, or an active optical sensor, accommodating a power source and actively providing an individualized optical locating signal irrespective of receiving light or not.

If the at least one tool sensor is an electromagnetic surgical tool sensor, the surgical tool sensor tracking system may be the same as the tumour sensor tracking system. If the at least one surgical tool sensor is an optical tool sensor, the surgical tool sensor tracking system may be an optical tracking system comprising at least one camera, and is different from the tumour sensor tracking system.

If the at least one reference sensor is an electromagnetic reference sensor, the reference sensor tracking system may be the same as the tumour sensor tracking system. If the at least one reference sensor is an optical reference sensor, reference sensor tracking system is an optical tracking system comprising at least one camera, and is different from the tumour sensor tracking system.

The navigation software 202 comprises an image registration component 222 for registering of pre-operative images from the picture archiving system 204. A displaying component 224 processes data for visualization of anatomical structures, a tumour model representative of a tumour, and a surgical tool model representative of a surgical tool. A tumour model mapping component 226 is configured for mapping each tumour sensor location to a tumour model. A surgical tool mapping component 228 is configured for mapping each surgical tool sensor location to a surgical tool model. An anatomical structure mapping component 230 is configured for mapping each reference sensor location to at least one anatomical structure in the body of a patient.

With the navigation software 202, a real time visualization 232 of a tumour (as represented by the tumour model), a surgical tool (as represented by the surgical tool model) and an anatomical structure (as obtained by one or more of the imaging systems 214) may be performed on a display device.

In the implementation of FIG. 2, the at least one tumour sensor needs to be provided on or in or near the tumour in the human or animal body, and mapped to the tumour model before treatment or pre-operatively (steps 101 and 102 of the flow diagram of FIG. 1). Also the at least one reference sensor needs to be provided on the human or animal body, and mapped to an anatomical structure before treatment or pre-operatively, wherein the anatomical structure is, or has been scanned also (steps 121, 122 and 123 of the flow diagram of FIG. 1). Thereafter, the location of the at least one tumour sensor in space, and the location of the at least one reference sensor in space are determined before treatment or pre-operatively to be able to determine spatial relationships of tumour model and anatomical structure (steps 103 and 124 of the flow diagram of FIG. 1). After that, the implementation of FIG. 2 is ready for use during treatment or intra-operatively.

Figure 3:
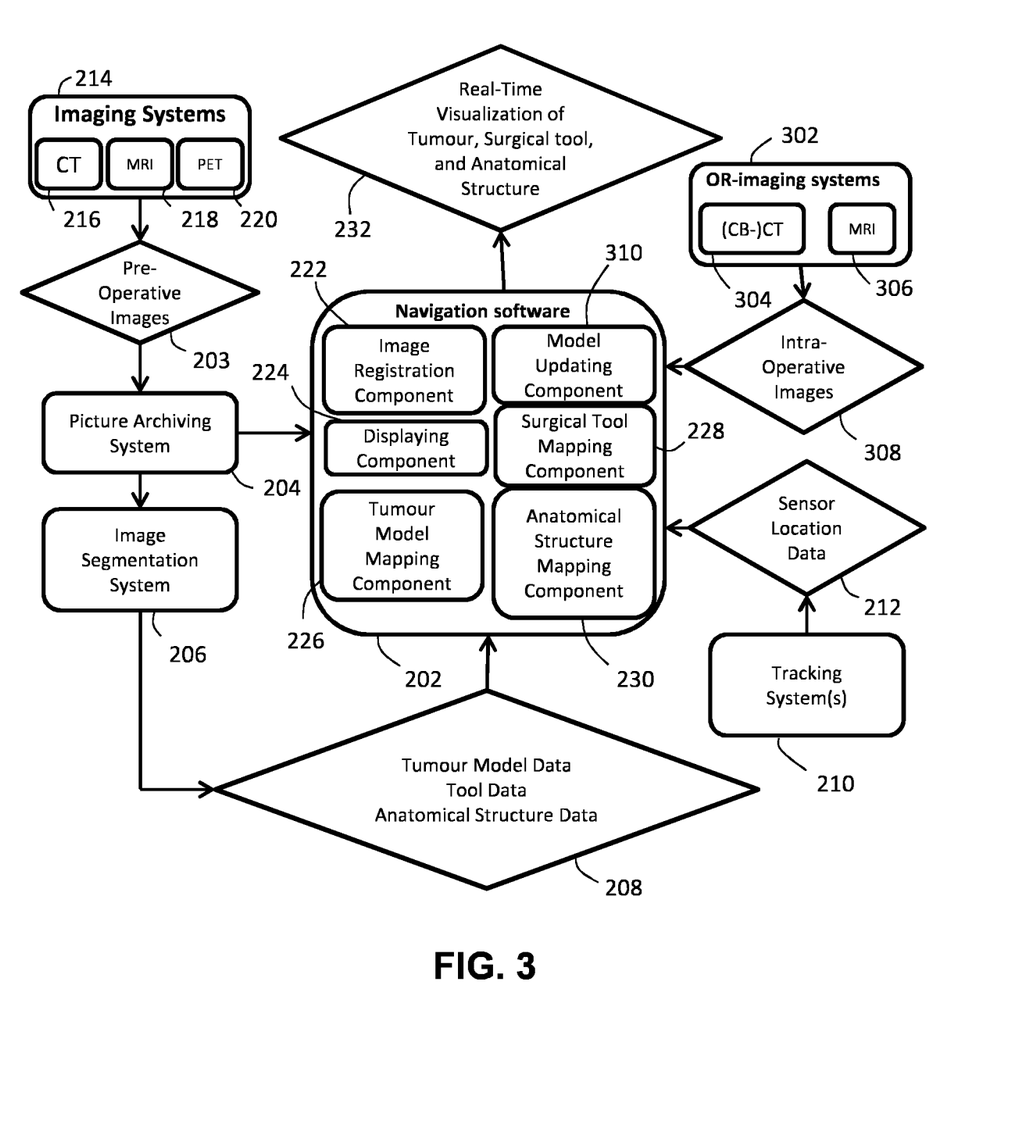
FIG. 3 depicts a diagram illustrating implementing aspects in a second embodiment of a method or system of the present invention.

FIG. 3 depicts a diagram illustrating implementing aspects in a second embodiment of a method or system of the present invention, providing added flexibility and information when used intra-operatively.

In an implementation of the method or system according to FIG. 3, navigation software 202 is used. The navigation software 202 receives input from four data sources.

A first data source for the navigation software 202 is a picture archiving system 204 containing image data of pre-operative images 203. The picture archiving system 204 receives image data representing pre-operative images 203 of anatomical structures from one or more imaging systems 214, such as a computer tomography, CT, imaging system 216, a magnetic resonance imaging, MRI, system 218, a positron emission tomography, PET, system 220, or any other appropriate system.

A second data source for the navigation software 202 is image segmentation system 206 comprising software providing image segmentation data 208 representing a tumour model, i.e. tumour model data, an anatomy model for a specific patient, i.e. anatomical structure data, and/or a surgical tool model, i.e. surgical tool model data.

A third data source for the navigation software 202 is a sensor tracking system 210, i.e. one or more of the tumour sensor tracking system, the surgical tool sensor tracking system, and the reference sensor tracking system, each tracking system providing sensor location data 212 of its respective sensor(s). The tumour sensor tracking system comprises a tumour sensor locating component configured for determining the location of each tumour sensor in space. The surgical tool sensor tracking system comprises a surgical tool sensor locating component configured for determining the location of each surgical tool sensor in space. The reference sensor tracking system comprises a reference sensor locating component configured for determining the location of each reference sensor in space.

A fourth data source for the navigation software 202 is image data representing intra-operative images 308 of anatomical structures from one or more Operation Room, OR, imaging systems 302, such as a (for example, cone beam, CB) computer tomography, CT, imaging system 304, a magnetic resonance imaging, MRI, system 306, or any other appropriate system. The MRI system 306 may be the same as MRI system 218.

It is noted here that a tumour sensor is an electromagnetic tumour sensor. A surgical tool sensor may be an electromagnetic surgical tool sensor or an optical surgical tool sensor. A reference sensor may be an electromagnetic reference sensor or an optical reference sensor.

An electromagnetic sensor may be a passive electromagnetic sensor, accommodating no power source and providing an individualized electromagnetic locating signal to a tracking system when interrogated by the tracking system, or an active electromagnetic sensor, accommodating a power source and actively providing an individualized electromagnetic locating signal to a tracking system without being interrogated by the tracking system.

An optical sensor may be a passive optical sensor, accommodating no power source and providing an individualized optical locating signal to a tracking system when receiving light, or an active optical sensor, accommodating a power source and actively providing an individualized optical locating signal irrespective of receiving light or not.

If the at least one surgical tool sensor is an electromagnetic surgical tool sensor, the surgical tool sensor tracking system may be the same as the tumour sensor tracking system. If the at least one surgical tool sensor is an optical surgical tool sensor, the surgical tool sensor tracking system may be an optical tracking system comprising at least one camera, and is different from the tumour sensor tracking system.

If the at least one reference sensor is an electromagnetic reference sensor, the reference sensor tracking system may be the same as the tumour sensor tracking system. If the at least one reference sensor is an optical reference sensor, reference sensor tracking system is an optical tracking system comprising at least one camera, and is different from the tumour sensor tracking system.

The navigation software 202 comprises an image registration component 222 for registering of pre-operative images from the picture archiving system 204. A displaying component 224 processes data for visualization of anatomical structures, a tumour model representative of a tumour, and a surgical tool model representative of a surgical tool. A tumour model mapping component 226 is configured for mapping each tumour sensor location to a tumour model. A surgical tool mapping component 228 is configured for mapping each surgical tool sensor location to a surgical tool model. An anatomical structure mapping component 230 is configured for mapping each reference sensor location to at least one anatomical structure in the body of a patient. A model updating component 310 receives data of intra-operative images 308 taken with one or more OR imaging systems 302. The model updating component 310 is configured to intra-operatively update the tumour model and/or the anatomical structure based on the intra-operative images 308 obtained.

With the navigation software 202, a real time visualization 232 of a tumour (as represented by the tumour model), a surgical tool (as represented by the surgical tool model) and an anatomical structure (as obtained by one or more of the imaging systems 214) may be performed on a display device.

In the implementation of FIG. 3, the at least one tumour sensor may be provided on or in or near the tumour in the human or animal body, and mapped to the tumour model, before treatment or pre-operatively, and also during treatment or intra-operatively due to the one or more OR imaging systems 302 providing intra-operative images 308 to model updating component 310 of the navigation software 202 (steps 101 and 102 of the flow diagram of FIG. 1). Also the at least one reference sensor may be provided on the human or animal body, and mapped to an anatomical structure, before treatment or pre-operatively, and also during treatment or intra-operatively, wherein the anatomical structure is scanned (steps 121, 122 and 123 of the flow diagram of FIG. 1). The location of the at least one tumour sensor in space, and the location of the at least one reference sensor in space may be determined pre-operatively, and also intra-operatively, to be able to determine spatial relationships of tumour model and anatomical structure (steps 103 and 124 of the flow diagram of FIG. 1).

Figure 4:
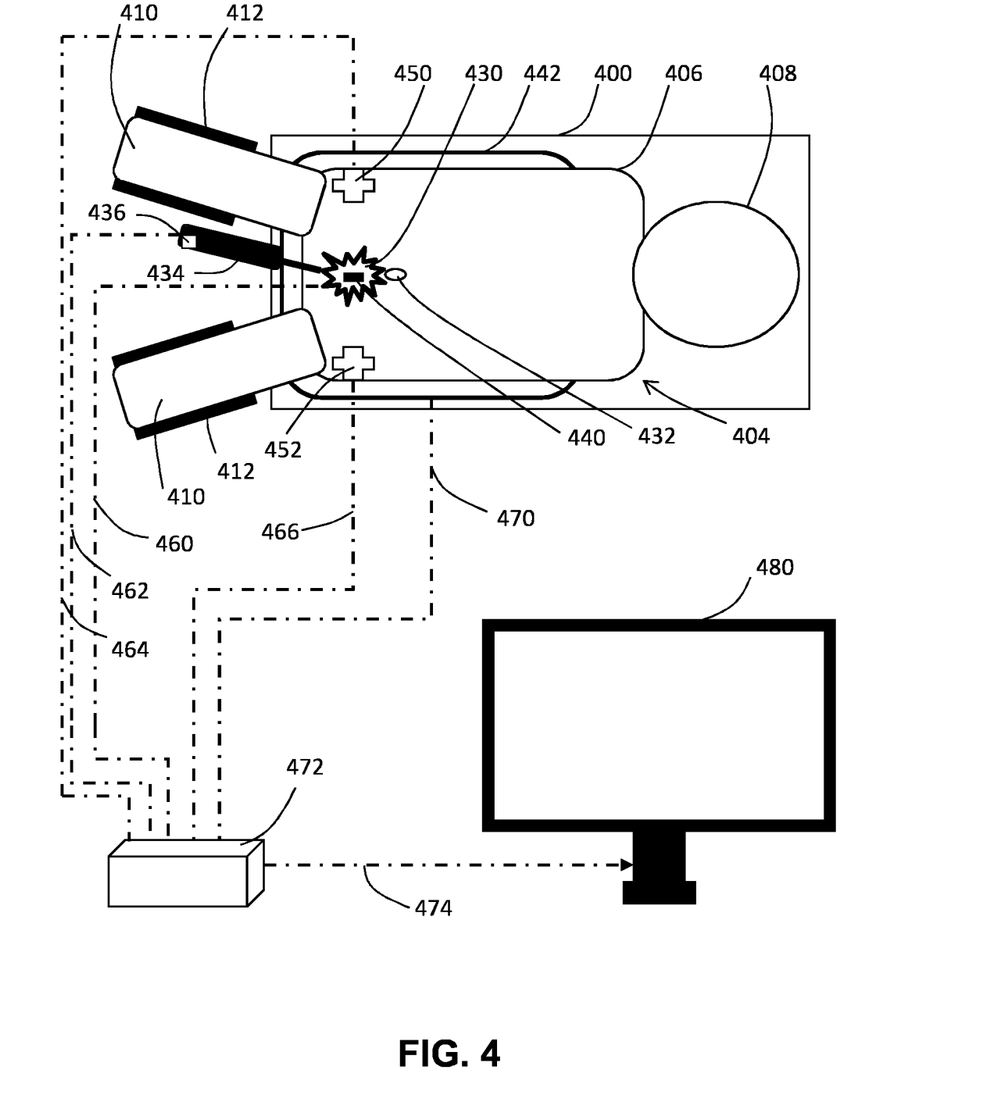
FIG. 4 schematically depicts different sensors and a sensor tracking system as applied in an embodiment of a method or system of the present invention.

FIG. 4 schematically depicts different sensors and a sensor tracking system 210 (see FIGS. 2, 3) as applied in an embodiment of a method or system of the present invention.

FIG. 4 shows a top view of an operation table 400 on which a human patient 404 is placed. A body 406 and head 408 of the patient 404 rest on the operation table 400. Legs 410 of the patient 404 rest on leg supports 412. The body 406 of the patient 404 has a tumour 430 under a body surface in the abdominal area. To reach the tumour 430, an incision 432 may be made with a surgical tool 434, such as a surgical knife.

At least one electromagnetic, EM, tumour sensor 440 has been provided on or in the tumour 430. Alternatively, the tumour sensor 440 may be provided in the vicinity of, or in close proximity to, the tumour 430. At least one EM reference sensor 450 (FIG. 4 showing two reference sensors 450, 452) is provided on the body 406 of the patient 404, such that each reference sensor 450, 452 has a spatial relationship to an internal anatomical structure of the patient 404 as well as possible. The reference sensors 450, 452 may be placed on the skin of the body 406 near the hip joints of the patient 404. In other embodiments, the reference sensors may be placed below the surface of the body 406. The surgical tool 434 is provided with at least one EM surgical tool sensor 436.

Below the patient 404, an electromagnetic, EM, field generator 442 is provided in the operation table 400. The EM generator 442 is configured to generate an electromagnetic field to cause each tumour sensor 440, reference sensor 450, 452, and surgical tool sensor 436 to provide a signal indicating its respective, location in space. The signal from each sensor 436, 440, 450, 452 is individualized to be able to discriminate between the sensors.

The respective location signals from each tumour sensor 440, reference sensor 450, 452, and surgical tool sensor 436 are tracked by a tracking system 472, such that the location and/or orientation of each sensor in space is available real-time, or quasi real-time. The location signals may be sent to the tracking system 472 wirelessly or through wires, as indicated in FIG. 4 by dash-dotted lines 460, 462, 464, 466. A dash-dotted line 470 indicates a wired or wireless connection from the tracking system 472 to the EM field generator 442.

As indicated by dash-dotted line 474, sensor location data 212 (see FIGS. 2, 3) indicating the location in space of each tumour sensor 440, reference sensor 450, 452, and surgical tool sensor 436 are transmitted to the navigation software system 202 (see FIGS. 2, 3). The navigation software system 202 provides a real-time or quasi real-time visualization of the tumour 430, the surgical tool 434 and an anatomical structure of the patient 404 in an image displayed by display device 480.

Figure 5:
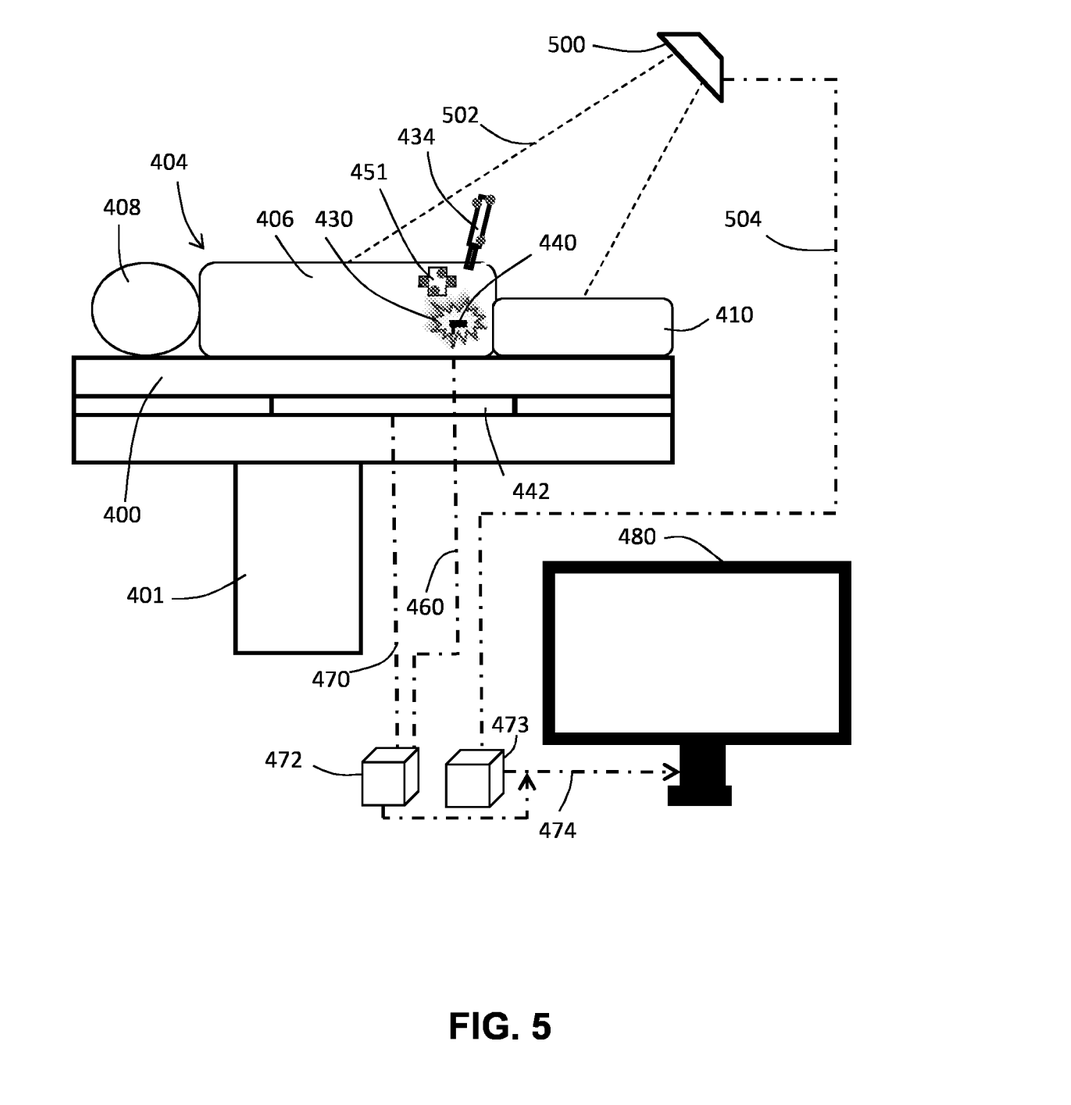
FIG. 5 schematically depicts different sensors and different tracking systems as applied in a further embodiment of a method or system of the present invention.

FIG. 5 schematically depicts different sensors and different tracking systems as applied in a further embodiment of a method or system of the present invention.

FIG. 5 shows a side view of an operation table 400 on a support 401. A human patient 404 is placed on the operation table 400. A body 406, head 408 and legs 410 of the patient 404 rest on the operation table 400. The body 406 of the patient 404 has a tumour 430 under a body surface in the abdominal area. To reach the tumour 430, a surgical tool 434, such as a surgical knife, is used. The surgical tool 434 may be handled by a surgeon or other physician, or may be operated by a robot (not shown).

At least one electromagnetic, EM, tumour sensor 440 is provided on or in or near the tumour 430. Alternatively, the tumour sensor 440 may be provided in the vicinity of, or in close proximity to, the tumour 430. At least one optical reference sensor 451 is provided on the body 406 of the patient 404, such that each reference sensor 451 has a spatial relationship to an internal anatomical structure of the patient 404 as well as possible. The at least one reference sensor 451 may be placed on the skin of the body 406 near the hip joints of the patient 404, or in the body 406 of the patient 404. The surgical tool 434 is provided with at least one optical surgical tool sensor 437.

Above the patient 404, an optical radiation transmitter/receiver 500 is provided covering an area indicated by dashed lines 502. The optical reference sensor 451 and the optical surgical tool sensor 436 both comprise optical reflectors and/or optical emitters, indicated by circles, so that the optical radiation transmitter/receiver 500 may provide location signals indicating the location of the sensors 451, 436 in space. The optical radiation transmitter/receiver 500 comprises a camera.

Below the patient 404, an electromagnetic, EM, field generator 442 is provided in the operation table 400. The EM generator 442 is configured to generate an electromagnetic field to cause each tumour sensor 440 to provide a signal indicating its respective location in space.

The location signals from each tumour sensor 440 are tracked by an EM tracking system 472, while the respective location signals from each reference sensor 451, and surgical tool sensor 437 are tracked by an optical tracking system 473, such that the location and/or orientation of each sensor in space is available real-time. The location signals may be sent to the EM tracking system 472 and the optical tracking system 473 wirelessly or through wires, as indicated in FIG. 5 by dash-dotted lines 460, 504. A dash-dotted line 470 indicates a wired or wireless connection from the tracking system 472 to the EM field generator 442.

As indicated by dash-dotted line 474, sensor location data 212 (see FIGS. 2, 3) indicating the location in space of each tumour sensor 440, reference sensor 450, 452, and surgical tool sensor 436 are transmitted to the navigation software system 202 (see FIGS. 2, 3) from the EM tracking system 472 and the optical tracking system 473. The navigation software system 202 provides a real-time visualization of the tumour 430, the surgical tool 434 and an anatomical structure of the patient 404 in an image displayed by display device 480.

Figure 6:
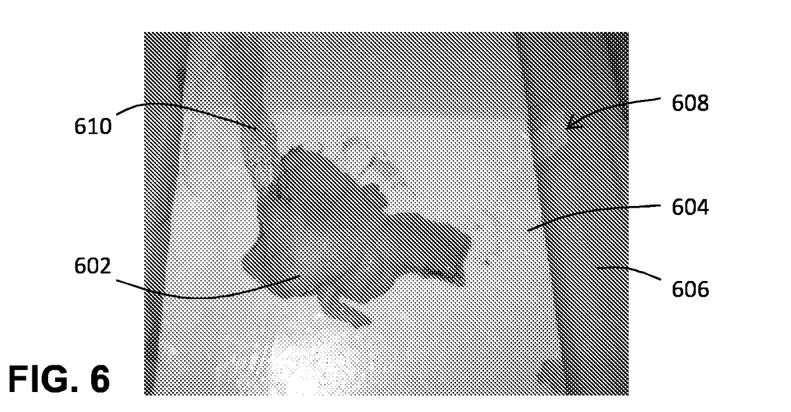
FIG. 6 shows a perspective view of an experimental arrangement of a body part.

FIG. 6 is a photograph showing a perspective view of an experimental arrangement of a body part 602 containing a tumour, or at least a tissue portion prepared to have physical properties different from surrounding tissues, which allows the tissue portion to be considered and detected as being a tumour or similar artifact for the sake of the experiment. Herein, reference is made to "tumour" indicating an actual tumour, said specifically prepared tissue portion or said artifact. The body part 602 has been placed in a box, in particular a box made from transparent plastic material. The box comprises a bottom wall and side walls 606 extending from the bottom wall. The body part 602 rests on a plastic support 604, which in turn rests on the bottom wall of the box.

The box is provided with a reference sensor 608 fixed to a side wall 606 at the outside thereof. The body part 602 is provided with a tumour sensor 706 (see FIGS. 7a, 7b) adjacent to the tumour. A sensor cable 610 from the tumour sensor 706 leads out of the box.

In the experimental arrangement, the box may be considered to simulate a human or animal body, in that the body part 602 is an anatomical structure taking a first spatial location and orientation relative to the box, and the tumour is "under the body surface". The reference sensor 608 is provided on a surface of the box, thus simulating placement thereof on a surface of the human or animal body.

Figure 7A:
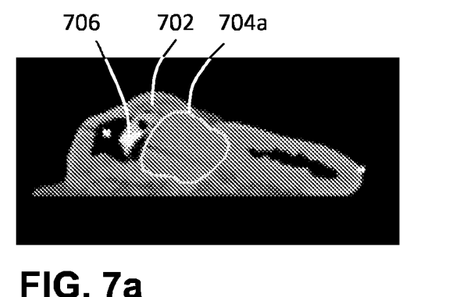
FIGS. 7a and 7b depict CT scans in different directions of the body part indicating a location of a tumour.
Figure 7B:
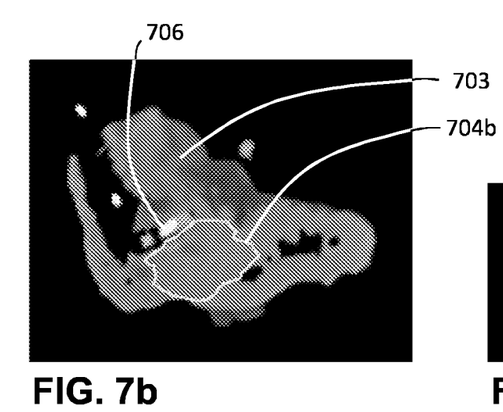

Referring to FIGS. 7a and 7b, the body part 602 was scanned in a computer tomography, CT, process, and the actual tumour location was determined. In FIG. 7a, showing a side view 702 of the body part 602 as obtained by the CT scan, a first contour 704a of the actual tumour from the particular first perspective is indicated. Also, the location of the tumour sensor 706 in the vicinity of the actual tumour is indicated. In FIG. 7b, showing a top view 703 of the body part 602 as obtained by the CT scan, a second contour 704b of the actual tumour from the particular second perspective is indicated.

The location of the reference sensor 608 in space was determined by interaction of the reference sensor 608 with a reference sensor tracking system (not shown), and the reference sensor 608 was mapped to the body part 602.

The location of the tumour sensor 706 in space was determined by interaction of the tumour sensor 706 with a tumour sensor tracking system (not shown).

Based on the first and second contours 704a and 704b, and possible other contours determined from other points of view, a digital volumetric tumour model, representative of the tumour, was determined, and the tumour sensor 706 was mapped to the tumour model.

Then, the body part 602 was moved in space, in particular shifted over several centimeters on the support 604, and rotated around a vertical axis.

Then, the location of the reference sensor 608 in space was determined, and the location of the tumour sensor 706 in space was determined by the tumour sensor tracking system.

A new CT scan of the body part 602 was acquired to confirm the accuracy of a projection of the tumour model.

Figure 8A:
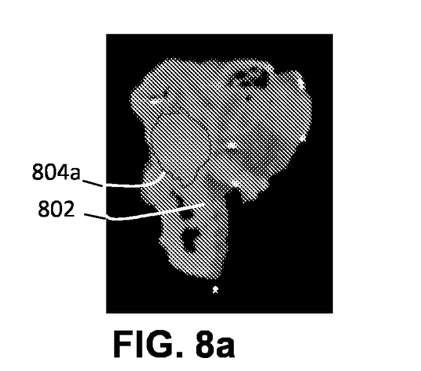
FIGS. 8a and 8b depict display views of the body part in different directions obtained with the method of the present invention, indicating the location of the tumour using a tumour model.
Figure 8B:
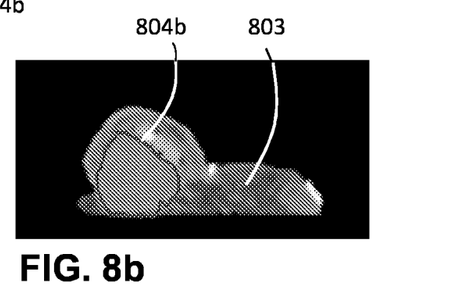

FIGS. 8a and 8b show virtual images which were then assembled, showing the tumour model, as located with the tumour sensor 706, in a spatial relationship to the body part 602, as located in the new CT scan. FIG. 8a shows a first contour 804a of the tumour model in a top view 802 of the body part 602 obtained by the new CT scan. FIG. 8b shows a second contour 804b of the tumour model in a side view 803 of the body part 602 obtained by the new CT scan.

Comparison of actual tumour contours, as determined with the new CT scan, with the first and second contours 804a, 804b, as determined from the tumour model, shows the tumour model and it location to be correct within 1.5 millimeters, thereby proving the applicability of the present invention to provide accurate visual information about a location of a tumour under a body surface of a human or animal body.

As explained in detail above, in a method and system for providing visual information about a tumour location in human or animal body, an electromagnetic tumour sensor is provided in the tumour and tracked to determine its location in space, which is mapped to a tumour model. A surgical tool sensor is provided on a surgical tool, and tracked to determine its location in space, which is mapped to a surgical tool model. The body is scanned to obtain information about an anatomical structure. A reference sensor is provided on the body, and tracked to determine its location in space, which is mapped to the anatomical structure. A virtual image is displayed showing the tumour model, located with the at least one tumour sensor, in spatial relationship to the surgical tool model, located with the at least one surgical tool sensor, and the anatomical structure, located with the at least one reference sensor.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather, to provide an understandable description of the invention.

The terms "a"/"an", as used herein, are defined as one or more than one. The term plurality, as used herein, is defined as two or more than two. The term another, as used herein, is defined as at least a second or more. The terms including and/or having, as used herein, are defined as comprising (i.e., open language, not excluding other elements or steps). Any reference signs in the claims should not be construed as limiting the scope of the claims or the invention.

The fact that certain measures are recited in mutually different dependent claims does not indicate that a combination of these measures cannot be used to advantage.

The term coupled, as used herein, is defined as connected, although not necessarily directly, and not necessarily mechanically.

A single processor or other unit may fulfil the functions of several items recited in the claims.

The terms computer program, software, and the like as used herein, are defined as a sequence of instructions designed for execution in a processor of a computer system. A program, computer program, or software application may include a subroutine, a function, a procedure, an object method, an object implementation, an executable application, an applet, a servlet, a source code, an object code, a shared library/dynamic load library and/or other sequence of instructions designed for execution on a computer system.

A computer program may be stored and/or distributed on a suitable medium, such as an optical storage medium or a solid-state medium supplied together with or as part of other hardware, but also be distributed in other forms, such as via the Internet or other wired or wireless telecommunication systems.

The invention claimed is:

1. A system for providing visual information about a location and shape of a tumour under a body surface of a human or animal body, the system comprising:
    at least one electromagnetic tumour sensor;
    a tumour sensor tracking system, wherein each tumour sensor is configured to interact with the tumour sensor tracking system to determine an individual location of the tumour sensor in space;
    a tumour model mapping component configured for mapping each tumour sensor location to a digital volumetric tumour model, wherein the tumour model comprises one or more volumes shaped to represent the shape of the tumour;
    a surgical tool provided with at least one surgical tool sensor;
    a surgical tool sensor tracking system, wherein each surgical tool sensor is configured to interact with the surgical tool sensor tracking system to determine an individual location of the surgical tool sensor in space, wherein the surgical tool sensor tracking system is calibrated to provide locations in a first coordinate system, and wherein the tumour sensor tracking system is calibrated to provide locations in a second coordinate system;
    a surgical tool mapping component configured for mapping each surgical tool sensor location to a digital surgical tool model representative of a shape of the surgical tool;
    an anatomical structure information input component for receiving information about at least one anatomical structure in the human or animal body different from the tumour;
    at least one reference sensor;
    a reference sensor tracking system, wherein each reference sensor is configured to interact with the reference sensor tracking system to determine an individual location of the reference sensor in space, wherein the reference sensor tracking system is calibrated to provide locations in a third coordinate system;
    an anatomical structure mapping component configured for mapping a position on the surface of the human or animal body determined by each reference sensor location to the at least one anatomical structure in the human or animal body;
    a tumour sensor locating component configured for determining the location of each tumour sensor in space;
    a surgical tool sensor locating component configured for determining the location of each surgical tool sensor in space;
    a reference sensor locating component configured for determining the location of each reference sensor in space,
    a display device; and
    a displaying component configured for displaying on the display device, based on the first and second coordinate systems, a virtual image assembled to show the digital volumetric tumour model, comprising said one or more volumes shaped to represent the shape of the tumour, as located with the at least one tumour sensor, in a spatial relationship to the digital surgical tool model representative of the shape of the surgical tool, as located with the at least one surgical tool sensor,
    wherein the displaying component is configured for assembling, based on the third coordinate system, the virtual image further to show the at least one anatomical structure, as located with the at least one reference sensor, in a spatial relationship to the digital volumetric tumour model, comprising said one or more volumes shaped to represent the shape of the tumour, as located with the at least one tumour sensor, and in a spatial relationship to the digital surgical tool model representative of the shape of the surgical tool, as located with the at least one surgical tool sensor.

2. The system according to claim 1, wherein the at least one tumour sensor is configured to communicate wirelessly or wired with the tumour sensor tracking system.

3. The system according to claim 1, wherein the at least one surgical tool sensor is configured to communicate wirelessly or wired with the surgical tool sensor tracking system.

4. The system according to claim 1, wherein the at least one reference sensor is configured to communicate wirelessly or wired with the reference sensor tracking system.

5. The system according to claim 1, wherein the at least one surgical tool sensor is an electromagnetic surgical tool sensor, and wherein the surgical tool sensor tracking system is the same as the tumour sensor tracking system.

6. The system according to claim 1, wherein the at least one surgical tool sensor is an optical surgical tool sensor, and wherein the surgical tool sensor tracking system is an optical tracking system comprising at least one camera.

7. The system according to claim 1, wherein the at least one reference sensor is an electromagnetic reference sensor, and wherein the reference sensor tracking system is the same as the tumour sensor tracking system.

8. The system according to claim 1, wherein the at least one reference sensor is an optical reference sensor, and wherein the reference sensor tracking system is an optical tracking system comprising at least one camera.

9. The system according to claim 1, further comprising a model updating component configured to receive data of images and update the tumour model or the anatomical structure based on the images obtained.

10. The system according to claim 1, wherein the at least one tumour sensor further is configured to interact with the tumour sensor tracking system to determine an individual orientation of the tumour sensor in space.

11. The system according to claim 1, wherein the at least one surgical tool sensor further is configured to interact with the surgical tool sensor tracking system to determine an individual orientation of the surgical tool sensor in space.

12. The system according to claim 1, wherein the at least one reference sensor further is configured to interact with the reference sensor tracking system to determine an individual orientation of the reference sensor in space.

13. The system according to claim 1, wherein the displaying component is configured to assemble the virtual image further to show a scale of length, or a scaled distance between the tumour model and the surgical tool model.

14. The system according to claim 1, wherein the displaying component is configured to assemble the virtual image further to show a scale of length, or a scaled distance between the tumour model and the anatomical structure.

15. The system according to claim 1, wherein the displaying component is configured to assemble the virtual image further to show a scale of length, or a scaled distance between the surgical tool model and the anatomical structure.

16. The system according to claim 1, wherein the one or more volumes of the tumour model are shaped according to a contour of the tumour.

17. The system according to claim 1, wherein the tumour model further comprises a body tissue layer around the shape of the tumour.

18. A method of providing visual information about a location of a tumour under a body surface of a human or animal body with the system of claim 1, the method comprising:
interacting, by the tumour sensor tracking system, with the at least one electromagnetic tumour sensor to determine the individual location of the tumour sensor in space;
determining the digital volumetric tumour model representative of the shape of the tumour;
mapping each tumour sensor location to the tumour model;
providing the at least one surgical tool provided with the at least one surgical tool sensor, the at least one surgical tool sensor interacting with the surgical tool sensor tracking system to determine the individual location of the surgical tool sensor in space;
determining the digital surgical tool model representative of the shape of the surgical tool;
mapping each surgical tool sensor location to the surgical tool model;
scanning the human or animal body to obtain information about at least one anatomical structure in the human or animal body different from the tumour;
interacting, by the reference sensor tracking system, with the at least one reference sensor located on the surface of the human or animal body to determine the individual location of the reference sensor in space;
mapping each reference sensor location to at least one anatomical structure in the human or animal body;
determining the location of each tumour sensor in space;
determining the location of each surgical tool sensor in space;
determining the location of each reference sensor in space;
assembling, based on the first and second coordinate systems, the virtual image showing the digital volumetric tumour model representative of the shape of the tumour, as located with the at least one tumour sensor, in the spatial relationship to the digital surgical tool model representative of the shape of the surgical tool, as located with the at least one surgical tool sensor; and
assembling, based on the third coordinate system, the virtual image further to show the at least one anatomical structure, as located with the at least one reference sensor, in the spatial relationship to the digital volumetric tumour model representative of the shape of the tumour, as located with the at least one tumour sensor, and in the spatial relationship to the digital surgical tool model representative of the shape of the surgical tool, as located with the at least one surgical tool sensor.

19. The method according to claim 18, wherein the at least one surgical tool sensor is an electromagnetic surgical tool sensor, and wherein the surgical tool sensor tracking system is the same as the tumour sensor tracking system; or
wherein the at least one surgical tool sensor is an optical surgical tool sensor, and wherein the surgical tool sensor tracking system is an optical tracking system comprising at least one camera.

20. The method according to claim 18, wherein the at least one reference sensor is an electromagnetic reference sensor, and wherein the reference sensor tracking system is the same as the tumour sensor tracking system; or
wherein the at least one reference sensor is an optical reference sensor, and wherein the reference sensor tracking system is an optical tracking system comprising at least one camera.

21. A non-transitory computer readable medium for providing visual information about a location and shape of a tumour under a body surface of a human or animal body comprising instructions which, when loaded in a processor, cause the processor to operate;
a tumour sensor tracking system configured to interact with one or more electromagnetic tumour sensors to determine an individual location of each of the tumour sensors in space;
a tumour model mapping component to map each tumour sensor location to a digital volumetric tumour model, wherein the tumour model comprises one or more volumes shaped to represent the shape of the tumour;

a surgical tool sensor tracking system configured to interact with at least one surgical tool sensor of a provided surgical tool to determine an individual location of the surgical tool sensor in space, wherein the surgical tool sensor tracking system is calibrated to provide locations in a first coordinate system, and wherein the tumour sensor tracking system is calibrated to provide locations in a second coordinate system;

a surgical tool mapping component to map each surgical tool sensor location to a digital surgical tool model representative of a shape of the surgical tool;

an anatomical structure information input component to receive information about at least one anatomical structure in the human or animal body different from the tumour;

a reference sensor tracking system configured to interact with one or more reference sensors to determine an individual location of each reference sensor in space, wherein the reference sensor tracking system is calibrated to provide locations in a third coordinate system;

an anatomical structure mapping component to map a position on the surface of the human or animal body determined by each reference sensor location to the at least one anatomical structure in the human or animal body;

a tumour sensor locating component to determine the location of each tumour sensor in space;

a surgical tool sensor locating component to determine the location of each surgical tool sensor in space;

a reference sensor locating component to determine the location of each reference sensor in space; and a displaying component to display on a display device, based on the first and second coordinate systems, a virtual image assembled to show the digital volumetric tumour model, comprising said one or more volumes shaped to represent the shape of the tumour, as located with the at least one tumour sensor, in a spatial relationship to the digital surgical tool model representative of the shape of the surgical tool, as located with the at least one surgical tool sensor, wherein the displaying component is configured for assembling, based on the third coordinate system, the virtual image further to show the at least one anatomical structure, as located with the at least one reference sensor, in a spatial relationship to the digital volumetric tumour model, comprising said one or more volumes shaped to represent the shape of the tumour, as located with the at least one tumour sensor, and in a spatial relationship to the digital surgical tool model representative of the shape of the surgical tool, as located with the at least one surgical tool sensor.

* * * * *